United States Patent [19]
DeCosse

[11] Patent Number: 5,655,824
[45] Date of Patent: Aug. 12, 1997

[54] AMBULANCE CABINETS

[75] Inventor: Gary A. DeCosse, St. Paul, Minn.

[73] Assignee: Road Rescue, Inc., St. Paul, Minn.

[21] Appl. No.: 558,025

[22] Filed: Nov. 13, 1995

[51] Int. Cl.$^6$ ................................................. A61B 19/02
[52] U.S. Cl. ......................... 312/209; 312/352; 52/717.03
[58] Field of Search ............................... 52/716.3, 717.03,
52/717.04, 717.05; 108/35, 34, 27; 220/448,
444, 406, 461; 312/209, 258, 204, 352;
206/586

[56]  References Cited

U.S. PATENT DOCUMENTS

| | | | |
|---|---|---|---|
| 2,047,747 | 7/1936 | Schemmel | 52/716.3 |
| 5,236,390 | 8/1993 | Young . | |
| 5,496,609 | 3/1996 | Michelstein | 52/717.03 |

Primary Examiner—Peter M. Cuomo
Assistant Examiner—Gerald A. Anderson
Attorney, Agent, or Firm—Jacobson & Johnson

[57]  ABSTRACT

A rigid cabinet for storing supplies, with the cabinet projecting outward into an area where personnel move about while attending to a patient with the rigid cabinet having a corner region with a recess therein having a resilient member located in the recess to form a cushioned corner on the rigid cabinet and a flexible exterior covering on the cabinet, with the exterior covering having a surface free of crevices as to provide a continuous exterior cabinet surface that can be wiped clean of contamination with the corner region of the cabinet formed by the combination of the flexible exterior covering and the resilient member to thereby provide cushioning to minimize injury to a person who might accidently bump into the corner region of the cabinet.

8 Claims, 1 Drawing Sheet

AMBULANCE CABINETS

FIELD OF THE INVENTION

This invention relates generally to emergency vehicles, and more specifically to emergency vehicles that have compartments where ill or injured patients are attended to as they are transported to medical facilities.

BACKGROUND OF THE INVENTION

In general, emergency vehicles have a patient compartment with a patient area where medical personnel attend to ill or injured persons. In order to provide a working area to enable the medical personnel to attend to the ill or injured persons, there are usually provided cabinets for the storage of medical supplies. The cabinets project or protrude out from the walls or floors of the compartments. One of the hazards of such protrusions is that the medical personnel can accidently bump into the corners as they move about in the moving vehicle, which might cause serious injury to the medical personnel. This problem is exacerbated by the fact the ambulance might brake quickly or make sharp turns which can cause the ambulance personnel to accidently bump into the corners of any protrusion within the ambulance compartment. A further problem is that in the compartment where ill or injured persons are attended to, the compartment must be cleaned of contamination each time an ill or injured person is attended to in the compartment.

SUMMARY OF THE INVENTION

A rigid cabinet for storing supplies, with the cabinet projecting outward into an area where personnel move about while attending to a patient with the rigid cabinet having a corner region with a recess therein having a resilient member located in the recess to form a cushioned corner to the rigid cabinet and a flexible exterior covering on the cabinet, with the exterior covering having a surface free of crevices as to provide a continuous exterior cabinet surface that can be wiped clean of contamination, further, with the corner region of the cabinet formed by the combination of the flexible exterior covering and the resilient member to thereby provide cushioning to minimize injury to a person who might accidently bump into the corner region of the cabinet.

DESCRIPTION OF THE PREFERRED EMBODIMENT

Figure 1:
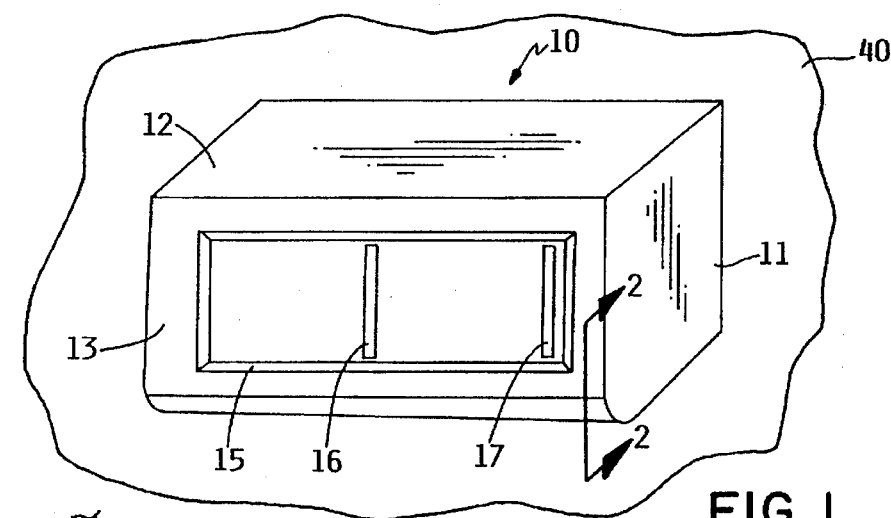
FIG. 1 shows a perspective view of a cabinet having the cleanable protective corners of the present invention.

Referring to FIG. 1 reference numeral 10 identifies a rigid cabinet 10 mounted on a wall 40 of an ambulance compartment for the transportation and administration of emergency care to an ill or injured person. Cabinet 10 includes a surface 12, a first side surface 11, and a second side surface (not shown). Extending from the front of cabinet 10 and under cabinet 10 is an exterior covering 13. Exterior covering 13 is a polymer plastic material that has an exterior surface that can be easily wiped free of contamination from germs or bacteria. A commercially available material sold under the trademark Kydex.

A first laterally slidable door 16 is mounted in frame 15 to provide ingress and egress to the inside of cabinet 10. Similarly, A second laterally slideable door 17 is mounted in frame 15 to also provide ingress and egress to the inside of cabinet 10.

Figure 2:
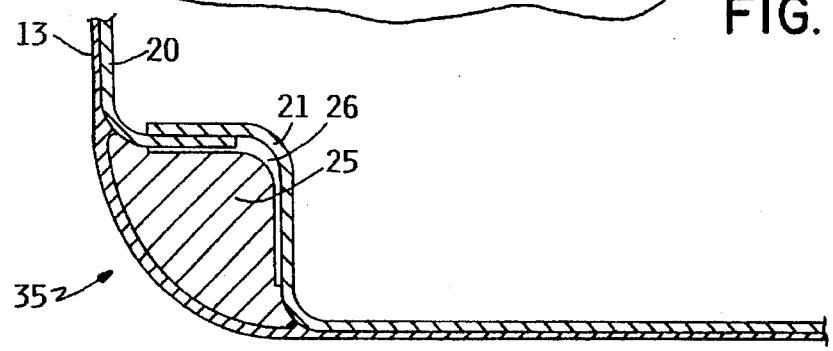
FIG. 2 shows a cross sectional view taken along lines 2—2 of FIG. 1 to reveal the interior construction of the cleanable protective corners.

FIG. 2 shows a cross sectional view of the corner region of cabinet 10 with a recess therein. That is, rigid cabinet frame members 21 and 20 are joined to each other by spot welding or the like with the corner junction formed by the two members projecting inward to form recess 26. An elongated resilient member 25 is located in recess 26 to form a rounded corner 35 to the rigid cabinet 10. The resilient member 25 is characterized by having sufficient compressibility so as to compress inward in response to a force thereon. Located on the outside of cabinet 10 is a flexible exterior covering 13 which has a surface free of crevices or cracks to enable the surface to be cleaned of contaminates such as bacteria and germs by wiping with a cloth. The exterior covering 14 extends seamlessly over rigid cabinet 10 and over resilient member 25 to provide a continuous exterior cabinet surface that can be wiped clean of contamination with the corner cushioned region of cabinet formed by the combination of the flexible exterior covering and the resilient member. Exterior covering 13 is fastened to rigid cabinet frame members 20 and 21 with an adhesive or the like.

Figure 3:
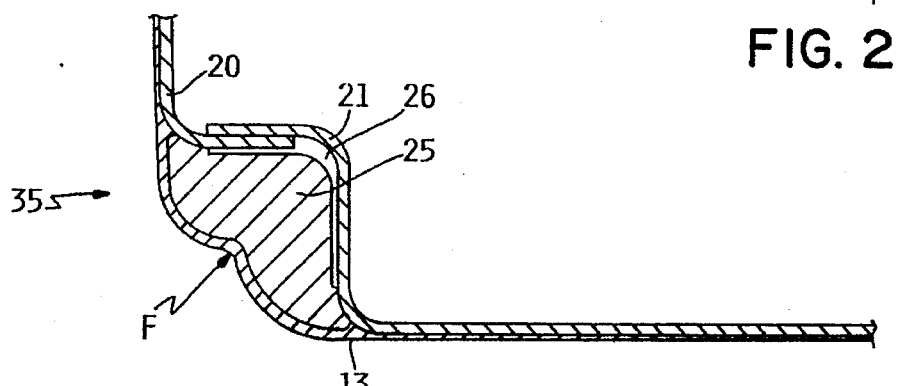
FIG. 3 shows the shock absorbing feature of the cleanable protective corner of FIG. 2.

FIG. 3 illustrates the condition where a force impacts on corner region 35. Note the force indicated by "F" forces flexible exterior covering 13 inward and at the same time compresses resilient member 25. The effect is to provide cushioning to minimize injury to a person who might accidently bump into the corner region of the cabinet. In addition, the incorporation of the resilient member into the cabinet eliminates the problem of having to replace padded corners as the corners become an integral part of the cabinet and are not detachable due to wear and tear of the patient compartment. Consequently, the cushion corner of the present invention becomes a corner easily cleanable to provide infectious control as well as provide safety to personnel working or riding within the patient compartment.

Figure 4:
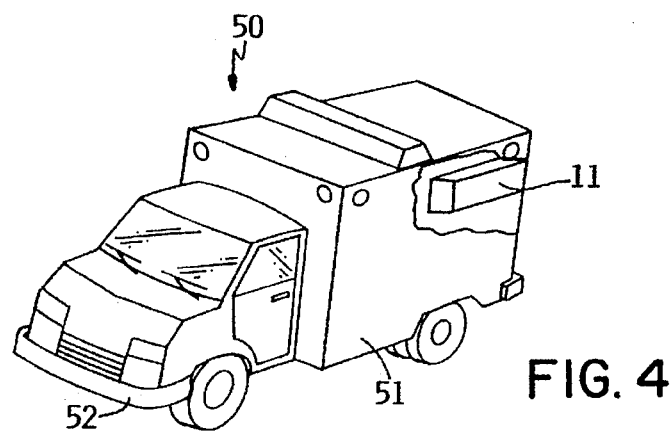
FIG. 4 shows an ambulance containing the present invention.

FIG. 4 shows ambulance 50 with track chassis 52 and a patient compartment 51 that is partially cut away to reveal cabinet 11 located in the patient compartment.

While the corner region of the cabinet has been shown as rounded it is apparent that the cleanable cushioned corner of the present invention can have other shapes. It is envisioned that any corner which protrudes from the ambulance compartment walls can be fined with my resilient corner to protect the ambulance personnel from unnecessary injury.

I claim:

1. An ambulance cabinet comprising:
   a rigid cabinet for storing supplies, said cabinet projecting outward into an area where personnel move about while attending to a patient, said rigid cabinet having a corner region with a recess therein;
   a resilient member located in said recess to form a rounded corner to the rigid cabinet, said resilient member having sufficient compressibility so as to compress inward in response to a force thereon;
   a flexible exterior covering on said cabinet, said exterior covering having a surface free of crevices to enable the surface to be cleaned by wiping with a cloth, said exterior covering extending seamlessly over said rigid cabinet and over said resilient member so as to provide a continuous exterior cabinet surface that can be wiped clean of contamination with the corner region of said cabinet formed by the combination of the flexible exterior covering and the resilient member providing cushioning to minimize injury to a person who might accidentally bump into the corner region of the cabinet.

2. The ambulance cabinet of claim 1 wherein the resilient member is extruded rubber.

3. The ambulance cabinet of claim 2 wherein the exterior covering is a polymer plastic material.

4. The ambulance cabinet of claim 3 wherein the rigid cabinet is made of metal.

5. The ambulance cabinet of claim 3 wherein the rigid cabinet is made of wood.

6. The ambulance cabinet of claim 1 wherein the resilient member extends in a longitudinal direction along said corner region.

7. The ambulance cabinet of claim 1 wherein the resilient member extends in a vertical direction along said corner region.

8. The ambulance cabinet of claim 1 wherein the resilient member is foam rubber and is adhesively fastened to said rigid cabinet.

* * * * *